(12) United States Patent
Nicaud et al.

(10) Patent No.: US 6,582,951 B1
(45) Date of Patent: Jun. 24, 2003

(54) METHOD FOR NON-HOMOLOGOUS TRANSFORMATION OF *YARROWIA LIPOLYTICA*

(75) Inventors: Jean-Marc Nicaud, Trappes (FR); Claude Gaillardin, Versailles (FR); Georges Pignede, Bois-Colombes (FR)

(73) Assignees: Institut National de la Recherche Agronomique - INRA, Paris (FR); Centre National de la Recherche Scientifique - CNRS, Paris (FR)

( * ) Notice: Subject to any disclaimer, the term of this patent is extended or adjusted under 35 U.S.C. 154(b) by 0 days.

(21) Appl. No.: 09/786,048

(22) PCT Filed: Sep. 1, 1999

(86) PCT No.: PCT/FR99/02079
§ 371 (c)(1),
(2), (4) Date: Apr. 27, 2001

(87) PCT Pub. No.: WO00/12729
PCT Pub. Date: Mar. 9, 2000

(30) Foreign Application Priority Data

Sep. 1, 1998 (FR) .............................................. 98 10900

(51) Int. Cl.[7] .............................. C12N 1/20; C12N 1/14; C12N 1/15; C12N 1/16; C12N 15/00; C12N 15/74
(52) U.S. Cl. ................. 435/254.2; 435/243; 435/252.3; 435/254.1; 435/440; 435/471; 435/473; 435/483; 435/484
(58) Field of Search .............................. 435/243, 252.3, 435/254.1, 254.11, 254.2, 440, 471, 473, 483, 484

(56) References Cited

FOREIGN PATENT DOCUMENTS

| EP | 0 138 508 | 4/1985 |
|---|---|---|
| EP | 0 220 864 | 5/1987 |

OTHER PUBLICATIONS

Barth and Gallardin, The dimorphic fungus Yarrowia lipolytica, In Non-conventional yeasts in biotechnology (Wolf K Ed.), Springer-Verlag, Berlin, pp. 313–388, 1996.*

C. Neuvéglise, et al., Gene, vol. 213, pp. 37–46, "A Shuttle Mutagenesis System for Tagging Genes in the Yeast Yarrowia Lipolytica", 1998.

M–T. Le Dall, et al., Current Genetics, vol. 26, pp. 38–44, "Multiple–Copy Integration in the Yeast Yarrowia Lipolytica", 1994.

N. Schmid–Berger, et al., Journal of Bacteriology, vol. 176, No. 9, pp. 2477–2482, "Ylt1, A Highly Repetitive Retrotransposon in the Genome of the Dimorphic Fungus Yarrowia Lipolytica", May 1994.

* cited by examiner

*Primary Examiner*—Rebecca E. Prouty
*Assistant Examiner*—Manjunath N. Rao
(74) *Attorney, Agent, or Firm*—Oblon, Spivak, McClelland, Maier & Neustadt, P.C.

(57) ABSTRACT

The invention concerns the integration of a gene of interest into the genome of a Yarrowia strain devoid of zeta sequences, by transforming said strain using a vector bearing zeta sequences.

21 Claims, 4 Drawing Sheets

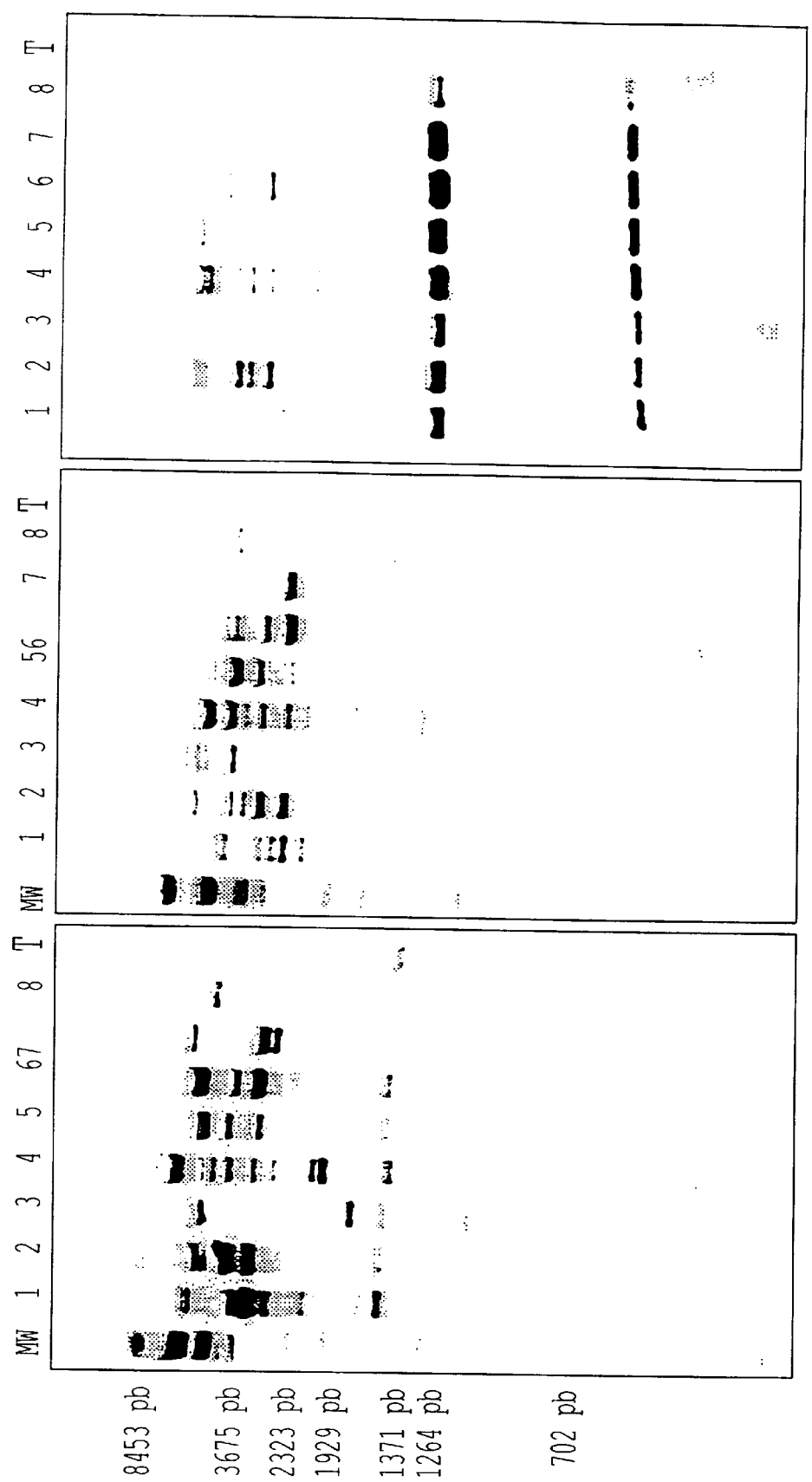

METHOD FOR NON-HOMOLOGOUS TRANSFORMATION OF *YARROWIA LIPOLYTICA*

The invention relates to tools for expressing heterologous genes in *Yarrowia lipolytica*.

The yeast *Y. lipolytica* is being increasingly used as a host for expressing genes of interest; in this context, "integrating" vectors, which allow the insertion of a segment of DNA bearing the gene of interest into the chromosomal DNA, are in particular used. For example, Application EP 138 508 discloses the transformation of *Yarrowia lipolytica* using vectors capable of integrating into the chromosomal DNA by recombination of *Y. lipolytica* sequences borne by said vectors, with the homologous sequences present on the chromosomal DNA of the host cell.

Among the *Yarrowia lipolytica* sequences used for constructing integrating vectors, mention will be made in particular of the sequences termed: "zeta sequences", which correspond to the LTRs (long terminal repeats) of the Ylt1 retrotransposon of *Yarrowia lipolytica*; these sequences have been described by SCHMID-BERGER et al. [J. Bacteriol., 2477–2482 (1994)], who indicate that they are present at a high copy number (approximately 35 copies of the complete retrotransposon and approximately 30 copies of the isolated zeta sequence) in the chromosomal DNA of certain strains of *Yarrowia lipolytica*. When a vector containing an insert flanked by zeta sequences is used to transform one of these strains of Yarrowia, the insert DNA integrates by homologous recombination with zeta sequences of the chromosomal DNA. In this way, transformed Yarrowia cells containing several copies of a heterologous sequence, integrated in tandem at chromosomal zeta sites, are obtained.

The inventors have now noted that, surprisingly, when vectors bearing inserts flanked by zeta sequences are used to transform Yarrowia cells lacking these sequences, the insert DNA integrates, however, into the chromosomal DNA, in the form of several copies dispersed in the genome.

A subject of the present invention is a method for integrating a gene of interest into the genome of a strain of Yarrowia, using a recombinant vector bearing an insert flanked by zeta sequences and comprising said gene of interest, which method is characterized in that said recombinant vector is used to transform a strain of Yarrowia, the genome of which lacks zeta sequences.

BRIEF DESCRIPTION OF THE FIGURES

FIG. 3: results obtained for the PO1d transformants.

Figure 1:
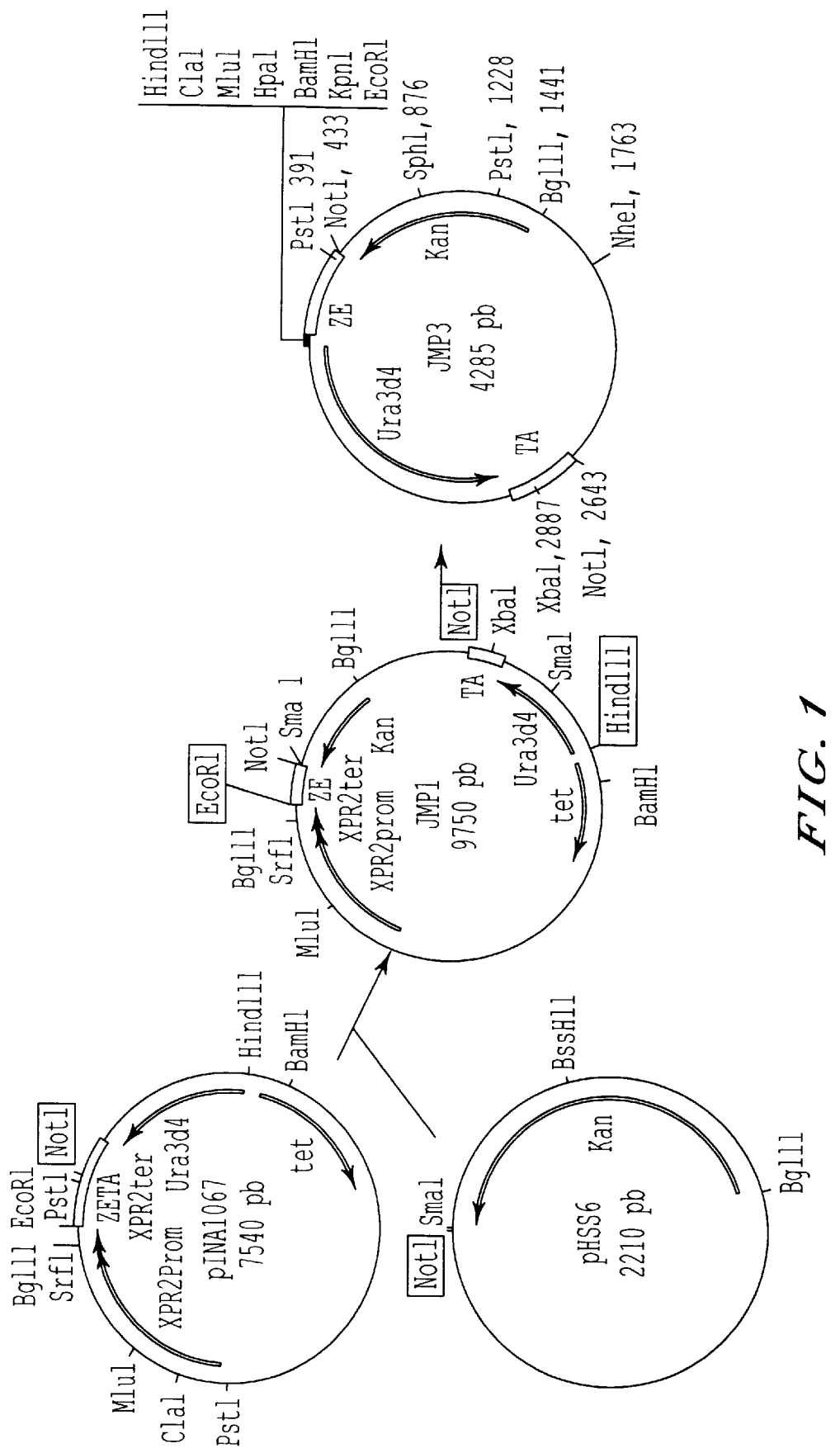
FIG. 1: construction of the JMP3 vector.

Strains of *Yarrowia lipolytica* lacking zeta sequences, which can be used for implementing the method in accordance with the invention, are, for example, the strains derived from the strain W29 (ATCC 20460 or CLIB 89, MatA), such as W29ura3-302 (CLIB 141, MatA Ura3-302), PO1a (CLIB 140, MatA Ura3-302, Leu2-270) and PO1d (CLIB 139, MatA Ura3-302, Leu2-270, xpr2-322), which are described by BARTH and GAILLARDIN [The dimorphic fungus *Yarrowia lipolytica*. In: *Non conventional yeasts in biotechnology* (Wolf K. Ed.). Springer-Verlag, Berlin, pp. 313–388 (1996)], and which can be obtained from the CLIB (Collection de Levures d'intérêt Biotechnologique [Collection of yeasts of biotechnological interest], INRA, Centre de Grignon, BP01, 78850 Thiberval-Grignon). Other strains which may be used can easily be selected based on the absence of signals of hybridization with nucleic acid probes derived from the zeta sequences.

According to a preferred embodiment of the method in accordance with the invention, the insert comprising the gene of interest also comprises sequences allowing the control of the expression of said gene and/or at least one marker for selection of the transformants.

The selection marker consists of a gene whose expression allows the selection of the transformants. It can be, for example, a gene for resistance to an antibiotic, or a mutant defective for a gene required for yeast growth, such as URA3, LEU2, etc. Advantageously, a selection marker will be chosen which needs to be present in several copies in order to be functional, thereby making it possible to select the transformants which have integrated several copies of the gene of interest. For example, use may be made, as a selection marker, of a defective URA3 marker, which is derived from the URA3 gene of *Y. lipolytica*, which allows complementation of auxotrophy for uracil, such as the URA3d markers described by LE DALL et al. [Curr. Genet., 26, 38–44 (1994)].

The sequences for controlling the expression are, in particular, promoter and terminator sequences which are active in Yarrowia. Use may be made of an inducible or constitutive promoter.

Very advantageously, use may also be made, as control sequences, of the promoter of the acyl CoA oxidase gene ACO2 of *Yarrowia lipolytica* [LE CLAINCHE, doctoral thesis from the Institut National Agronomique Paris Grignon [National Agronomic Institute Paris Grignon], defended on Jul. 2, 1997], or the promoter and/or terminator of the acid-resistant extracellular lipase gene LIP2 of *Yarrowia lipolytica*, disclosed in the French application under the name of LABORATOIRES MAYLOY-SPINDLER, entitled: "CLONAGE ET EXPRESSION DE LIPASES EXTRACELLULAIRES ACIDORESISTANTES DE LEVURES" [Cloning and expression of acid-resistant extracellular lipases of yeasts], filed on the same day as the present application.

The ACO2 and LIP2 promoters can both be induced with triglycerides and fatty acids.

Other selection markers and control sequences which can be used for implementing the present invention are, for example, those cited by BARTH and GAILLARDIN (abovementioned publication).

When the product of the gene of interest is intended to be secreted by the host cell, said insert also comprises signals for controlling the secretion of said product. For this purpose, use may be made of signal sequences which are functional in *Yarrowia lipolytica*, for example all or part of the prepro sequence of the LIP2 gene disclosed in the abovementioned French application under the name of LABORATOIRES MAYOLY-SPINDLER.

A subject of the present invention is also transformed Yarrowia cells which can be obtained using the method in accordance with the invention. Advantageously, these transformed cells comprise at least two copies of the insert flanked by zeta sequences, comprising the gene of interest, integrated into their genome in a dispersed manner.

The present invention will be more fully understood with the aid of the further description which will follow, which refers to nonlimiting examples for obtaining transformed strains of *Yarrowia lipolytica* in accordance with the invention.

EXAMPLE 1

Construction of Vectors Comprising a ZETA Sequence

These vectors are obtained from the vector pINA1067, derived from a vector of type pINA970 described by BARTH and GAILLARDIN (abovementioned publication, FIG. 6), by excision of the portion of sequence between the XPR2 promoter and terminator, which was replaced with a linker containing the SrfI and BglII restriction sites. pINA1067 bears the defective URA3 marker ura3d4 described by LE DALL et al. (abovementioned publication), and also a tetracycline resistance marker.

The plasmid pHSS6 bearing an origin of replication for *E. coli* and a kanamycin resistance gene is linearized by restriction with NotI, and introduced into the NotI site of pINA1067. The ligation mixture is used to transform *E. coli*. The transformants which have integrated the plasmid are selected on tetracycline (6 mg/l) and kanamycin (40 mg/l).

The resulting vector, termed JMP1, is cleaved with HindIII and EcoRI, which eliminates the fragment bearing the XPR2 promoter and terminator sequences and the tetracycline resistance marker; this fragment is replaced with a polylinker which contains the HindIII, ClaI, MluI, HpaI, BamHI and EcoRI restriction sites.

The resulting vector is termed JMP3. A diagram of the various steps in the construction of JMP3 is given in FIG. 1.

The self-cloning vectors JMP3 and JMP5 integrate into the genome after cleavage with the NotI restriction enzyme. This restriction allows the elimination of the bacterial portion (origin of replication of *E. coli* and of the KanR resistance marker).

EXAMPLE 2
Construction of Expression Vectors

Expression vectors comprising a sequence encoding the acid-resistant extracellular lipase of *Yarrowia lipolytica*, disclosed in the abovementioned French application under the name of LABORATOIRES MAYOLY-SPINDLER, under the control of the ACO2 promoter (vector JMP6) or of its own promoter (vector JMP10), were constructed.

Vector JMP6

The promoter of the acyl CoA oxidase gene ACO2 was amplified by PCR using the total genomic DNA of *Y. lipolytica*, with the oligonucleotides Aco2P1 and Aco2P2, which contain a ClaI site and a HindIII site respectively.

Aco2P1:
   5' GCG ATCGAT CATACTGTTACACTGCTCCG 3' (SEQ ID NO: 1)

Aco2P2:
   5' GTGGGATCCGAAAGCTTCATGGCGTCGT-TGCTTGTGTGATTTTTGAGG 3' (SEQ ID NO: 2)

The 2168 bp PCR fragment was cloned into the EcoRV site of the vector BLUESCRIPT KS+. The resulting plasmid is called KS-ACO2prom. This vector was digested with ClaI and partially with HindIII so as to obtain a 2155bp fragment containing the complete ACO2 promoter.

In addition, a 1134bp HindIII-EcoRI fragment containing the sequence encoding the prolipase LIP2, and also the transcription terminator, was isolated from the plasmid termed pKS+-LIP2W29a. The two purified fragments were fused and inserted into the ClaI-EcoRI sites of the vector JMP3. The resulting plasmid is called JMP6.

Vector JMP10

A 2030 bp NdeI*-HindIII fragment containing the promoter of the lipase gene of *Y. lipolytica* was isolated from the plasmid termed pKS+-LIP2prom. For this, the plasmid pKS+-LIP2prom was digested with NdeI, and then treated with T4 DNA polymerase so as to make the NdeI site blunt (NdeI*). After inactivation of the NdeI enzyme and of the polymerase, the DNA was cleaved with HindIII. The 2030 bp NdeI*-HindIII fragment was ligated with the 1134 bp HindIII-EcoRI fragment bearing the lipase gene and its terminator, and the ligation product was inserted into the HpaI-EcoRI sites of the vector JMP3. The resulting plasmid is called JMP10.

Figure 2:
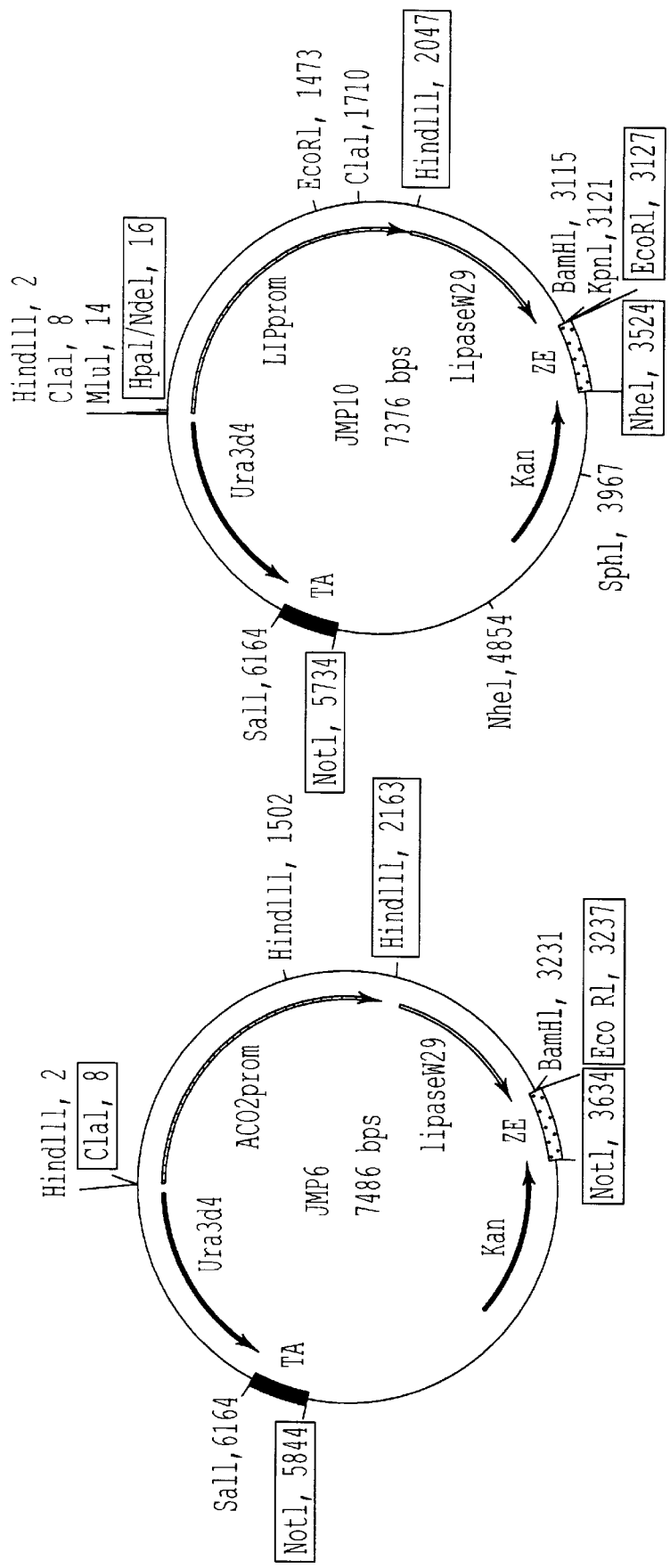
FIG. 2: the plasmids JMP6 and JMP10.

FIG. 2 represents the plasmids JMP6 and JMP10.

EXAMPLE 3
Production of *Y. lipolytica* Transformants

The following strains of *Y. lipolytica*, having a deletion of the URA3 gene, were used:
   PO1d: (CLIB 139, MatA Ura3-302, Leu2-270, xpr2-322), lacking zeta sequences;
   E150: (CLIB 122, MatA Ura3-302, Leu2-270, xpr2-322, his-1) having several copies of zeta sequences.

These two strains, described by BARTH and GAILLARDIN (abovementioned publication), are available from the CLIB.

The plasmids JMP6 and JMP10, linearized beforehand with NotI, which makes it possible to eliminate the sequences originating from the plasmid pHSS6, are introduced into the Yarrowia cells by transformation with lithium acetate, according to the protocol described by BARTH and GAILLARDIN.

20 to 50 transformants/µg of DNA are usually obtained with the strain PO1d, and 100 to 200 transformants/µg of DNA with the strain E150.

The various transformants will be referred to hereinafter according to the following nomenclature: strain name—plasmid number—transformant number. For example; PO1d-6-15=strain PO1d, plasmid JMP6, transformant number 15.

The structure of the transformants was studied by Southern transfer. The total genomic DNA of the strain of origin (T) and of the various transformants is digested with HindIII in the case of PO1d, and with BamHI (for the JMP6 transformants) or EcoRI (for the JMP10 transformants) in the case of E150.

The probes used are derived from the zeta sequences, from the sequence of the ACO2 promoter and from the sequence encoding the lipase LIP2.

The results obtained are illustrated in FIG. 3 for the PO1d transformants, and in FIG. 4 for the E150 transformants.

PO1d Transformants (JMP6)

FIG. 3A represents the results observed with the lipase probe; FIG. 3B represents the results observed with the ZETA probe; FIG. 3C represents the results observed with the ACO2 probe.

In the strain PO1d (line T), a 1.4 kb band is observed with the lipase probe, no band is observed with the zeta probe (absence of a zeta site in this strain) and a 1.1 kb band is observed with the ACO2 probe. In the case of the transformants, with the lipase and zeta probes, many bands of varying size are observed, corresponding to the number of copies and showing that they are dispersed in the genome.

In the case of the transformant strains in accordance with the invention, a non-homologous, multicopy and dispersed integration is therefore observed.

E150 Transformants (JMP6 and JMP10)

Figures 4A, 4B:
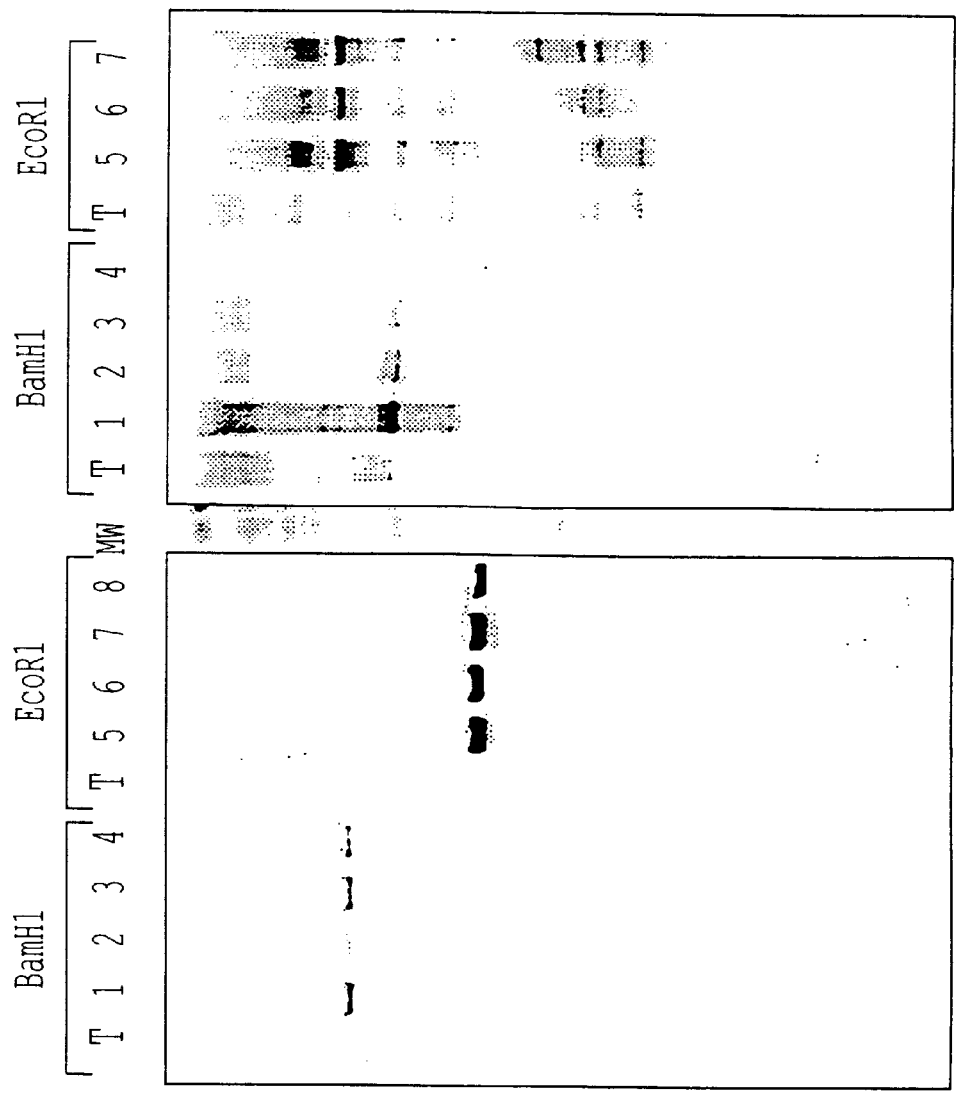
FIG. 4: results obtained for the E150 transformants.

FIG. 4A represents the results observed with the lipase probe+the ACO2 probe; FIG. 4B represents the results observed with the ZETA probe.

In FIG. 4A, in the transformants, amplification of the vector sequences is observed, revealed by the intensity of the 2.9 kb BamHI band (ACO2 promoter+lipase gene) or of the 1.6 kb EcoRI band (lipase gene), compared with that of the 2.6 kb genomic BamHI band which corresponds to the genomic ACO2 promoter, or that of the approximately 6 kb genomic EcoRI band which corresponds to the lipase gene.

In FIG. 4B, in the strain E150 and the transformants, several zeta sites are observed, revealed by many bands in the EcoRI restriction profile. The tandem integration is revealed by the intensity of the 2.5 kb BamHI band and the 3.7 kb EcoRI band, which correspond to the fragments expected if the sequences of the vectors are integrated in tandem.

In transformant 6, the disappearance of a zeta band is also noted, indicating the integration into this locus.

In the case of the strain E150 transformants, tandem integration by homologous integration at a zeta site is therefore observed.

Lipase Secretion by the Transformed Strains

Lipase production by the transformed strains was tested on various media. Both in the case of the strains in accordance with the invention derived from PO1d and in that of the comparison strains derived from E150, secretion at least ten to fifteen times greater than that of the nontransformed strains is observed.

signals for controlling the secretion of the product of said gene of interest.

6. Method according to claim 5, characterized in that said control signals comprise all or part of the prepro sequence of the acid-resistant extracellular lipase gene of *Yarrowia lipolytica*.

7. Transformed Yarrowia cell which can be obtained using a method according to claim 1.

8. Transformed cell according to claim 7, characterized in that it comprises at least 2 copies of the sequences of said vector, integrated into its genome in a dispersed manner.

9. The method of claim 1, wherein the transformed strain has at least two copies of said vector, integrated into its genome in a dispersed manner.

10. The method of claim 1, wherein the Yarrowia strain is *Yarrowia lipolytica*.

What is claimed is:

1. Method for integrating a gene of interest into the genome of a strain of Yarrowia, using a recombinant vector bearing an insert flanked by zeta sequences and comprising said gene of interest, characterized in that said recombinant vector is used to transform a strain of Yarrowia, the genome of which lacks zeta sequences.

2. Method according to claim 1, characterized in that the insert comprising the gene of interest also comprises sequences allowing the control of the expression of said gene and/or at least one marker for selection of the transformants.

3. Method according to claim 2, characterized in that said selection marker is a defective URA3 marker.

4. Method according to claim 2, characterized in that at least one of the sequences allowing the control of the expression of the gene of interest is chosen from: the promoter of the acyl CoA oxidase gene ACO2 of *Yarrowia lipolytica*, the promoter of the acid-resistant extracellular lipase gene of *Yarrowia lipolytica* and the terminator of the acid-resistant extracellular lipase gene of *Yarrowia lipolytica*.

5. Method according to claim 2, characterized in that said expression cassette also comprises a sequence encoding 11. The method of claim 10, wherein the Yarrowia strain is W29ura3-302, PO1a, or PO1d.

12. The transformed Yarrowia cell of claim 7, which is *Yarrowia lipolytica*.

13. The transformed Yarrowia cell of claim 12, wherein the Yarrowia strain W29ura3-302, PO1a, or PO1d is transformed.

14. Transformed Yarrowia cell which is obtained by the method of claim 2.

15. Transformed Yarrowia cell which is obtained by the method of claim 3.

16. Transformed Yarrowia cell which is obtained by the method of claim 4.

17. Transformed Yarrowia cell which is obtained by the method of claim 5.

18. Transformed Yarrowia cell which is obtained by the method of claim 6.

19. Transformed Yarrowia cell which is obtained by the method of claim 9.

20. Transformed Yarrowia cell which is obtained by the method of claim 10.

21. Transformed Yarrowia cell which is obtained by the method of claim 11.

\* \* \* \* \*

```
                         SEQUENCE LISTING

<160> NUMBER OF SEQ ID NOS: 2

<210> SEQ ID NO 1
<211> LENGTH: 29
<212> TYPE: DNA
<213> ORGANISM: Artificial Sequence
<220> FEATURE:
<223> OTHER INFORMATION: Synthetic DNA

<400> SEQUENCE: 1
gcgatcgatc atactgttac actgctccg                                    29

<210> SEQ ID NO 2
<211> LENGTH: 48
<212> TYPE: DNA
<213> ORGANISM: Artificial Sequence
<220> FEATURE:
<223> OTHER INFORMATION: Synthetic DNA

<400> SEQUENCE: 2
gtgggatccg aaagcttcat ggcgtcgttg cttgtgtgat ttttgagg               48
```